United States Patent
Yao

(10) Patent No.: US 10,229,766 B2
(45) Date of Patent: Mar. 12, 2019

(54) RADIATION FIELD CONTROL DEVICE AND NOVEL RADIOTHERAPY EQUIPMENT

(71) Applicant: SUZHOU LINATECH MEDICAL SCIENCE AND TECHNOLOGY CO., LTD., Industry Park Suzhou, Jiangsu (CN)

(72) Inventor: Jonathan Yi Yao, Jiangsu (CN)

(73) Assignee: Suzhou Linatech Medical Science and Technology Co., Ltd., Jiangsu (CN)

( * ) Notice: Subject to any disclaimer, the term of this patent is extended or adjusted under 35 U.S.C. 154(b) by 0 days.

(21) Appl. No.: 15/551,233

(22) PCT Filed: Dec. 30, 2015

(86) PCT No.: PCT/CN2015/100010
§ 371 (c)(1),
(2) Date: Aug. 15, 2017

(87) PCT Pub. No.: WO2016/155395
PCT Pub. Date: Oct. 6, 2016

(65) Prior Publication Data
US 2018/0033512 A1    Feb. 1, 2018

(30) Foreign Application Priority Data
Apr. 3, 2015   (CN) .......................... 2015 1 0155634

(51) Int. Cl.
*G21K 1/02*        (2006.01)
*A61N 5/10*        (2006.01)

(52) U.S. Cl.
CPC ............. *G21K 1/02* (2013.01); *A61N 5/1042* (2013.01); *A61N 5/1048* (2013.01); *A61N 2005/1095* (2013.01)

(58) Field of Classification Search
CPC ................................ G21K 1/02; A61N 5/1048
(Continued)

(56) References Cited

U.S. PATENT DOCUMENTS 5,672,878 A * 9/1997 Yao .......................... G01T 1/185
                                            250/385.1
5,866,914 A * 2/1999 Jones ....................... G21K 1/02
                                            250/505.1
(Continued)

FOREIGN PATENT DOCUMENTS

CN          2415779 Y      1/2001
CN          1537657 A      10/2004
(Continued)

OTHER PUBLICATIONS

An Office Action dated Sep. 23, 2016 in corresponding CN Application No. 201510155634.9 is attached.
(Continued)

*Primary Examiner* — Michael Maskell
(74) *Attorney, Agent, or Firm* — Muncy, Geissler, Olds & Lowe, P.C.

(57) ABSTRACT

The invention discloses a radiation field control device and radiotherapy equipment. Two or more different-sized light limiting barrels are directly machined on a light limiting barrel support, or two or more light limiting barrel mounting portions are arranged on the light limiting barrel support, then the two or more light limiting barrels are respectively mounted in the light limiting barrel mounting portions in a one-to-one correspondence manner, any one of the light limiting barrels can move to a working position through a light limiting barrel switching device, in this case, when the light limiting barrel having suitable size is required, the unsuitable light limiting barrel does not need to be detached, and the required light limiting barrel can be used conveniently and quickly by directly controlling the light limiting barrel switching device. By adopting the solution, the radiation field control device is not only simple in structure,
(Continued)

convenient and quick to use, but also greatly improves the working efficiency.

8 Claims, 3 Drawing Sheets

(58) Field of Classification Search
USPC .................................. 250/492.1–492.3, 505.1
See application file for complete search history.

(56) References Cited

U.S. PATENT DOCUMENTS

| | | | |
|---|---|---|---|
| 2006/0076515 A1* | 4/2006 | Matsuda | A61N 5/1043 250/492.23 |
| 2006/0293646 A1 | 12/2006 | Whayne et al. | |
| 2013/0221243 A1 | 8/2013 | Perkins | |
| 2013/0261430 A1 | 10/2013 | Uhlemann | |

FOREIGN PATENT DOCUMENTS

| | | |
|---|---|---|
| CN | 2932569 Y | 8/2007 |
| CN | 101032650 A | 9/2007 |
| CN | 102335484 A | 2/2012 |
| CN | 202620505 U | 12/2012 |
| CN | 103096974 A | 5/2013 |
| CN | 203598373 U * | 5/2014 |
| CN | 104338242 A | 2/2015 |
| CN | 104740784 A | 7/2015 |
| CN | 104740784 A | 7/2015 |
| CN | 204582309 U | 8/2015 |
| EP | 2641634 A1 | 9/2013 |
| JP | 2001170194 A | 6/2001 |
| WO | WO2009/055725 A1 | 4/2009 |

OTHER PUBLICATIONS

An Offce Action dated Jul. 6, 2017 in corresponding CN Application No. 201510155634.9 is attached.

* cited by examiner

RADIATION FIELD CONTROL DEVICE AND NOVEL RADIOTHERAPY EQUIPMENT

FIELD OF THE INVENTION

The present invention relates to a device used for manufacturing and application of a medical linear accelerator (linac), and it's mainly used for control of radiation field.

BACKGROUND OF THE INVENTION

With the development of tumor radiology and material science, radiotherapy has gradually entered the age of "three precisions" including precise positioning, precise planning and precise therapy as an important means for treating cancers. In the prior art, a light limiting barrel has the advantages of small penumbra and low influence on healthy sites. However, the radiation field of the light limiting barrel is generally round, so that the shape of a focus cannot be fitted well; besides, the shape and size of the light limiting barrel cannot be adjusted in real time. What's more, different-sized light limiting barrels need to be customized for different patients, so that the light limiting barrel is inconvenient to use and very troublesome to replace. In order to improve the working efficiency, in a latest solution of the prior art, a storage box is arranged beside an accelerator, a plurality of different-sized light limiting barrels are put into the storage box. When a light limiting barrel needs to be replaced for another size, the light limiting barrel below the accelerator should be taken down and put into the corresponding position of the storage box for storage and later use, and then, the light limiting barrel having the required size is taken out and mounted to the working position. The solution standardizes field management of the light limiting barrels and also improves the efficiency by taking and putting nearby, but the improvement on efficiency is still limited, in particular, when a light limiting barrel and a grating blade system are used simultaneously, the light limiting barrel is often mounted between the accelerator and the grating, and when the light limiting barrel needs to be replaced, the grating system is detached first and then a new grating is replaced and mounted, so that the operation is very tedious and there is also potential risk of equipment damage.

SUMMARY OF THE INVENTION

In order to solve the above problems, the present invention is aimed at providing an efficient and simple radiation field control device and novel radiotherapy equipment.

To fulfill the above aim, the present invention adopts the technical solution:

a radiation field control device, comprising:

a light limiting barrel support, wherein at least two light limiting barrels or at least two light limiting barrel mounting portions are arranged on the light limiting barrel support, the light limiting barrels are directly machined on the light limiting barrel support, and the light limiting barrel mounting portions are used for fixedly mounting or detachably mounting the light limiting barrels; and a light limiting barrel switching device, used for driving the light limiting barrel support to move, thus enabling any one of the light limiting barrels to move to a working position as required.

Two or more different-sizesd light limiting barrels are directly machined on the light limiting barrel support, or two or more light limiting barrel mounting portions are arranged on the light limiting barrel support, then the two or more light limiting barrels are respectively mounted in the light limiting barrel mounting portions in a one-to-one correspondence manner, any one of the light limiting barrels can move to the working position through the light limiting barrel switching device, in this case, when the light limiting barrel having suitable size is required, the unsuitable light limiting barrel does not need to be detached, and the required light limiting barrel can be used conveniently and quickly by directly controlling the light limiting barrel switching device. By adopting the solution, the radiation field control device is not only simple in structure, convenient and quick to use, but also greatly improves the working efficiency.

Further, the light limiting barrel support is linear, sector-shaped, ring-shaped or ray-shaped.

Further, the light limiting barrel support comprises a support body and detachable light limiting barrel mounting modules, and the light limiting barrel mounting portions are arranged on the light limiting barrel mounting modules.

Further, the light limiting barrel switching device comprises a guide rail and a driving device, the light limiting barrel support is mounted in a manner of matching with the guide rail and can slide freely along the guide rail, the driving device is connected with the light limiting barrel support in a transmission way and controls the light limiting barrel support to slide or stop on the guide rail, and the driving device comprises a motor and a gear set, or a pneumatic device, or a hydraulic device.

Further, the light limiting barrel switching device comprises a motor, a gear set and an output shaft, the light limiting barrel support comprises a support body and detachable light limiting barrel mounting modules, and the light limiting barrel mounting portions are arranged on the light limiting barrel mounting modules; the support body is connected with the output shaft and driven by the output shaft to rotate; the support body is provided with at least two module mounting portions around a rotating shaft thereof, and the light limiting barrel mounting modules are detachably connected with the module mounting portions in a matching manner.

Further, the module mounting portion is provided with a folding mechanism which can drive the module mounting portion and the light limiting barrel mounting module connected with the module mounting portion to be switched between the folding position and the working position.

Further, the module mounting portion or the light limiting barrel mounting module is provided with a telescopic mechanism, the telescopic mechanism can stretch to and fro along its axis, and at least two light limiting barrel mounting portions are arranged on each light limiting barrel mounting module.

Further, the light limiting barrel mounting module is provided with a lifting device which can drive the light limiting barrel to ascend or descend vertically, and the lifting device is a hydraulic device, a pneumatic device, an electromagnetic lifting device or a motor driven lifting device.

The present invention further provides novel radiotherapy equipment, comprising any one of the above-mentioned radiation field control devices.

Further, the radiation field control device is mounted between an accelerator and a grating of the novel radiotherapy equipment or mounted below the grating. The radiation field control device is matched with the grating, combines all advantages of the light limiting barrels and the grating and makes up the shortages of the both, and when a light limiting barrel is replaced, the grating does not need to be detached as in the prior art, so that the radiation field control device is simple and quick.

Figure 1:
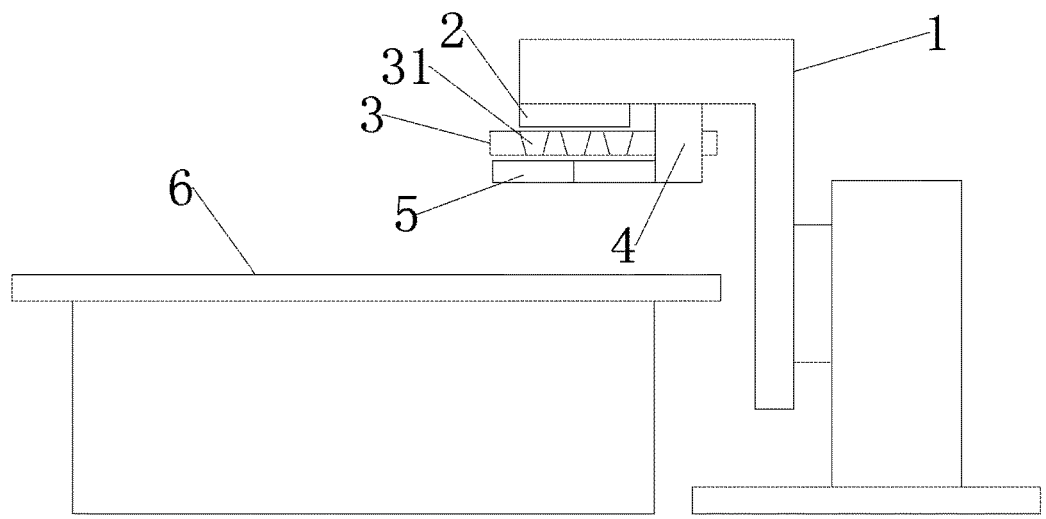
FIGS. 1-5 are schematic diagrams of the present invention.

Numbers and letters in the drawings express corresponding components:

1, large frame; 2, accelerator; 3, light limiting barrel support; 31, light limiting barrel; 4, light limiting barrel switching device; 41, rotating shaft; 5, grating blade device; 6, therapy bed.

DETAILED DESCRIPTION OF THE EMBODIMENTS

The present invention will be further described in detail below in combination with the accompanying drawings and specific embodiments.

Figure 2:
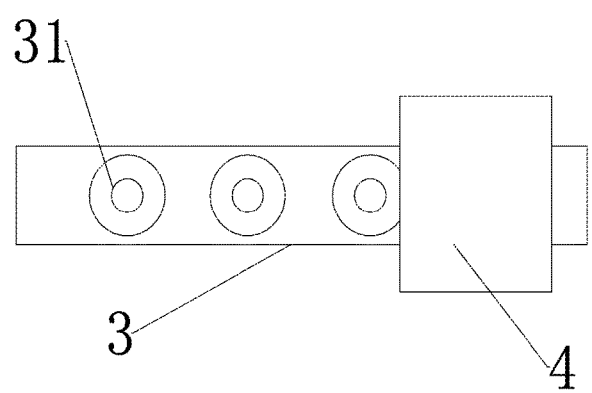

In one embodiment of the present invention, as shown in FIGS. 1 and 2, a radiation field control device comprises a light limiting barrel support 3 and a light limiting barrel switching device 4.

Three light limiting barrels 31 (or three light limiting barrel mounting portions) are arranged on the light limiting barrel support 3, the light limiting barrels are directly machined on the light limiting barrel support, and the light limiting barrel mounting portions are used for fixedly mounting or detachably mounting the light limiting barrels; the three different-sized light limiting barrels 31 are directly machined on the light limiting barrel support 3.

The light limiting barrel switching device 4 drives the light limiting barrel support 3 to move, thus enabling any one of the light limiting barrels 31 to move to a working position as required. The light limiting barrel switching device 4 shown in FIG. 1 comprises a supporting device fixed on a large frame 1 and further comprises a guide rail, a servo motor and a lead screw driving device (or an electromagnetic driving or hydraulic/pneumatic driving device) which are arranged on the supporting device, and the light limiting barrel support 3 is mounted on the guide rail in a sliding manner, connected with the servo motor and the lead screw driving device in a transmission way and driven by the servo motor and the lead screw driving device to horizontally slide to and fro.

Two or more different-sized light limiting barrels are directly machined on the light limiting barrel support, or two or more light limiting barrel mounting portions are arranged on the light limiting barrel support, then the two or more light limiting barrels are respectively mounted in the light limiting barrel mounting portions in a one-to-one correspondence manner, any one of the light limiting barrels can move to the working position through the light limiting barrel switching device, in this case, when the light limiting barrel having suitable size is required, the unsuitable light limiting barrel does not need to be detached, and the required light limiting barrel can be used conveniently and quickly by directly controlling the light limiting barrel switching device. By adopting the solution, the radiation field control device is not only simple in structure, convenient and quick to use, but also greatly improves the working efficiency. The positions of the light limiting barrels and the light limiting barrel mounting portions matched therewith can be digitally marked and stored into a control system, so that digital management and automatic switching operation can be conveniently realized.

As shown in the above drawings, the light limiting barrel support 3 is linear. In practical application, one set of the radiation field control devices can be adopted on single side, or two sets of radiation field control devices are horizontally opposed, so that the quantity of the light limiting barrels can be expanded, and switching inconvenience caused by too long individual light limiting barrel support can also be avoided. In some other embodiments, the light limiting barrel support may also be sector-shaped, ring-shaped (shown in FIG. 4) or ray-shaped (shown in FIG. 3).

In order to conveniently mount, maintain and replace the different-sized light limiting barrels, the light limiting barrel support can be further improved, the improved light limiting barrel support comprises a support body and detachable light limiting barrel mounting modules, and the light limiting barrel mounting portions are arranged on the light limiting barrel mounting modules. The light limiting barrel mounting modules may be rectangular, round, square or in other polygonal shape, the light limiting barrel support is provided with grooves matched with the light limiting barrel mounting modules and also provided with locking and fixing devices such as buckles or fixing guard plates, the light limiting barrel mounting modules can be mounted on and detached from the light limiting barrel support in the horizontal direction without influencing other components of equipment, and the light limiting barrels are mounted into the light limiting barrel mounting modules after the light limiting barrel mounting modules are taken down, so the light limiting barrels are very convenient and can be conveniently replaced, and the usage size range of the light limiting barrels of the equipment is expanded.

In the linear radiation field control device, the light limiting barrel switching device comprises a guide rail and a driving device, the light limiting barrel support is mounted in a manner of matching with the guide rail and can slide freely along the guide rail, the driving device is connected with the light limiting barrel support in a transmission way and controls the light limiting barrel support to slide or stop on the guide rail, and the driving device comprises a motor and a gear set, or a pneumatic device, or a hydraulic device.

Figure 5:
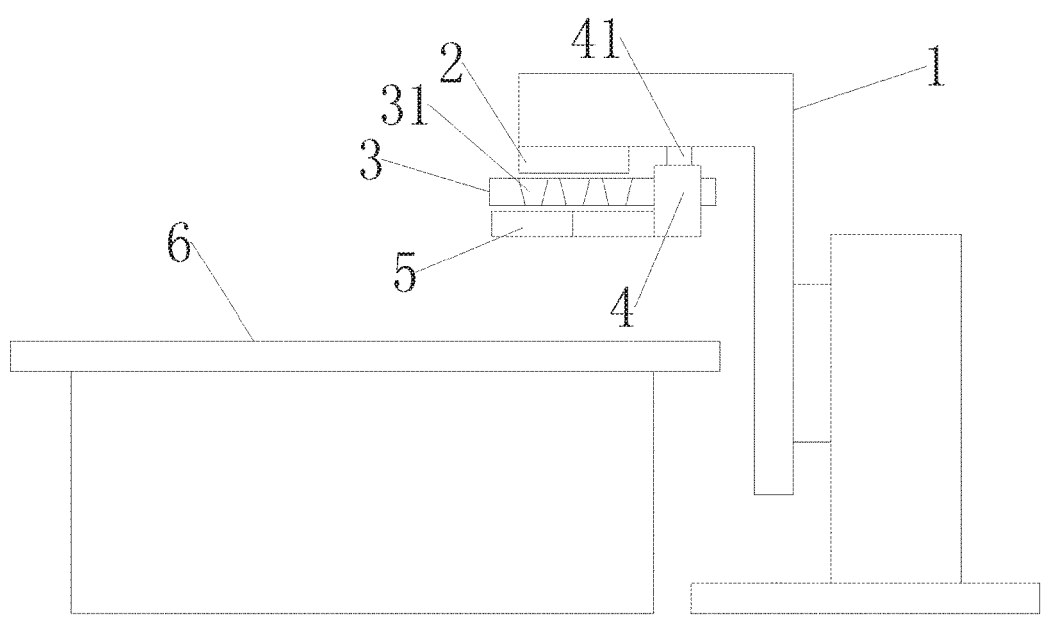

In order to facilitate mounting and maintenance, the radiation field control device can also be mounted on a rotating shaft, as shown in FIG. 5, the rotating shaft 41 can be driven by a special driving device to rotate horizontally, in this case, the light limiting barrel support 3 can rotate horizontally and move out the position of a grating blade 5 and an accelerator 2, so that unhindered mounting or maintenance can be performed.

Figure 3:
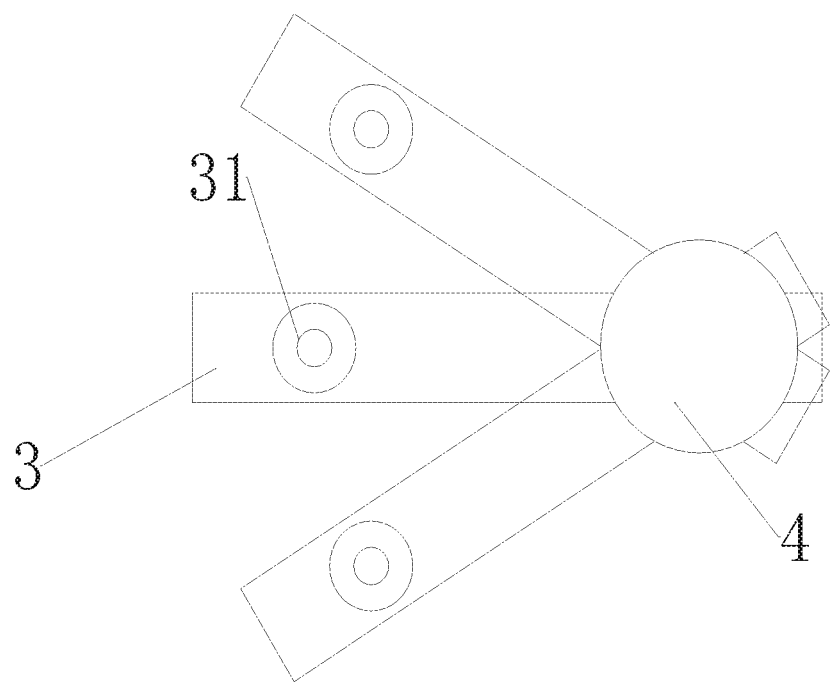
Figure 4:
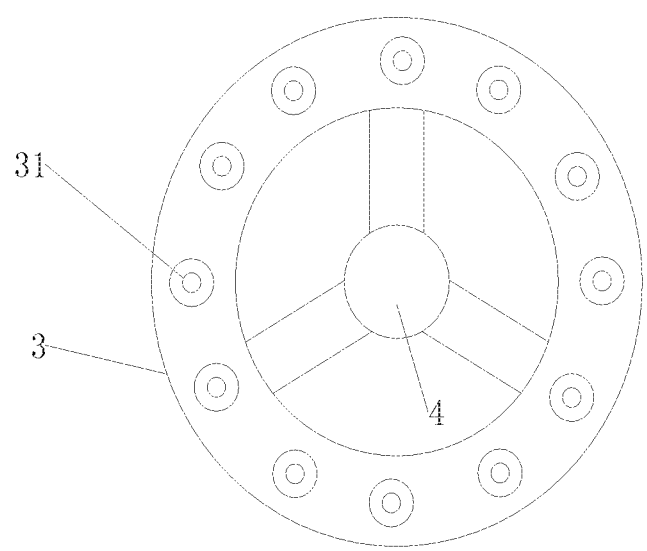

In practical application, the light limiting barrel switching device comprises a motor, a gear set and an output shaft, the light limiting barrel support comprises a support body and detachable light limiting barrel mounting modules, and the light limiting barrel mounting portions are arranged on the light limiting barrel mounting modules; the support body is connected with the output shaft and driven by the output shaft to rotate; the support body is provided with at least two module mounting portions around a rotating shaft thereof, and the light limiting barrel mounting modules are detachably connected with the module mounting portions in a matching manner. As shown in FIG. 3, the light limiting barrel support 3 is composed of three linear support bodies, each support body is provided with a light limiting barrel mounting portion for mounting a light limiting barrel (or directly machined with a light limiting barrel or a light limiting barrel mounting module), the distances between the centers of all the light limiting barrels and a rotating shaft of the whole radiation field control device are equal, i.e., all the light limiting barrels run around the same circle, and when the light limiting barrel switching device 4 rotates, one of the three light limiting barrels 31 can be conveyed to the working position. The quantity of the linear bodies can be one, two, three, four or random. Or, the light limiting barrel support may directly be ring-shaped as shown in FIG. 4, or is of a sector-shaped structure made from a portion of the ring.

In order to avoid interference or facilitate maintenance of the equipment under some situations, the module mounting portion is provided with a folding mechanism which can drive the module mounting portion and the light limiting barrel mounting module connected with the module mounting portion to be switched between the folding position and the working position. The linear support body can be turned over linearly or folded approximately vertically as required, thereby reducing the space occupied by the whole radiation control device.

Based on an example of FIG. 3, in order to further expand the quantity of the light limiting barrels, the module mounting portion or the light limiting barrel mounting module is provided with a telescopic mechanism, the telescopic mechanism can stretch to and fro along its axis, and at least two light limiting barrel mounting portions are arranged on each light limiting barrel mounting module. Thus, two or more light limiting barrels can be mounted on the support body, the light limiting barrel having required size can be switched by rotating and stretching as required, and the quantity of the light limiting barrels can be multiplied.

In order to control the radiation field more accurately to optimally match the different-sized light limiting barrels with the equipment and simultaneously in order to provide a lifting function in other required occasions, the light limiting barrel mounting module is provided with a lifting device which can drive the light limiting barrel to ascend or descend vertically, and the lifting device is a hydraulic device, a pneumatic device, an electromagnetic lifting device or a motor driven lifting device.

The present invention further provides novel radiotherapy equipment, comprising any one of the above-mentioned radiation field control devices.

Further, the radiation field control device is mounted between an accelerator and a grating of the novel radiotherapy equipment or mounted below the grating. The radiation field control device is matched with the grating, combines all advantages of the light limiting barrels and the grating and makes up the shortages of the both, and when a light limiting barrel is replaced, the grating does not need to be detached as in the prior art, so that the radiation field control device is simple and quick.

FIGS. 1 and 5 can be schematic diagrams of the whole radiotherapy equipment, wherein 1 designates a large frame, 2 designates an accelerator, 5 designates a grating blade device, and 6 designates a therapy bed. Other signs are as mentioned above.

The solution can also very conveniently realize intelligent control and realize automatic switching; a data storage device and a central control device can be additionally arranged, an identification code can be set for each light limiting barrel, the position of each light limiting barrel can be marked, the positions of the light limiting barrels and the light limiting barrel mounting portions matched therewith can be digitally marked and stored into the data storage device, and the central control device, according to the light limiting barrel having the required size, calls the digital code at the position of the light limiting barrel, and directly drives the required light limiting barrel to move to the working position through the light limiting barrel switching device. Thus, digital management and automatic switching operation can be conveniently realized.

Described above are merely preferred embodiments of the present invention. It should be pointed out that many modifications and improvements can also be made for those of ordinary skill in the art without departing from the concept of the present invention. These modifications and improvements fall into the protection scope of the present invention.

The invention claimed is:

1. A radiation field control device, comprising:
   a light limiting barrel support, wherein at least two light limiting barrels or at least two light limiting barrel mounting portions are arranged on the light limiting barrel support, the light limiting barrels are directly machined on the light limiting barrel support, and the light limiting barrel mounting portions are used for fixedly mounting or detachably mounting the light limiting barrels; and
   a light limiting barrel switching device, used for driving the light limiting barrel support to move, thus enabling any one of the light limiting barrels to move to a working position as required,
   wherein the light limiting barrel support is linear, sector-shaped, ring-shaped or ray-shaped, the light limiting barrel switching device comprises a guide rail and a driving device, the light limiting barrel support is mounted in a manner of matching with the guide rail and can slide freely along the guide rail, the driving device is connected with the light limiting barrel support in a transmission way and controls the light limiting barrel support to slide or stop on the guide rail, and the driving device comprises a motor and a gear set, or a pneumatic device, or a hydraulic device.

2. The radiation field control device of claim 1, wherein the light limiting barrel support comprises a support body and detachable light limiting barrel mounting modules, and the light limiting barrel mounting portions are arranged on the light limiting barrel mounting modules.

3. The radiation field control device of claim 1, wherein the light limiting barrel switching device comprises a motor, a gear set and an output shaft, the light limiting barrel support comprises a support body and detachable light limiting barrel mounting modules, and the light limiting barrel mounting portions are arranged on the light limiting barrel mounting modules; the support body is connected with the output shaft and driven by the output shaft to rotate; the support body is provided with at least two module mounting portions around a rotating shaft thereof, and the light limiting barrel mounting modules are detachably connected with the module mounting portions in a matching manner.

4. The radiation field control device of claim 3, wherein the module mounting portion is provided with a folding mechanism which can drive the module mounting portion and the light limiting barrel mounting module connected with the module mounting portion to be switched between the folding position and the working position.

5. The radiation field control device of claim 1, wherein the module mounting portion or the light limiting barrel mounting module is provided with a telescopic mechanism, the telescopic mechanism can stretch to and fro along its axis, and at least two light limiting barrel mounting portions are arranged on each light limiting barrel mounting module.

6. The radiation field control device of claim 3, wherein the light limiting barrel mounting module is provided with a lifting device which can drive the light limiting barrel to ascend or descend vertically, and the lifting device is a hydraulic device, a pneumatic device, an electromagnetic lifting device or a motor driven lifting device.

7. A radiotherapy equipment, comprising the radiation field control device of claim 1.

8. The radiotherapy equipment of claim 7, wherein the radiation field control device is mounted between an accelerator and a grating of the novel radiotherapy equipment or mounted below the grating.

* * * * *